United States Patent
Huang et al.

(10) Patent No.: US 8,573,060 B2
(45) Date of Patent: Nov. 5, 2013

(54) PARTICLE FOCUSING WITHIN A MICROFLUIDIC DEVICE USING SURFACE ACOUSTIC WAVES

(75) Inventors: Tony Jun Huang, State College, PA (US); Jingie Shi, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 754 days.

(21) Appl. No.: 12/631,059

(22) Filed: Dec. 4, 2009

(65) Prior Publication Data
US 2010/0139377 A1 Jun. 10, 2010

Related U.S. Application Data

(60) Provisional application No. 61/200,958, filed on Dec. 5, 2008.

(51) Int. Cl.
G01N 15/14 (2006.01)
G01N 29/02 (2006.01)

(52) U.S. Cl.
USPC ........................................ 73/570.5; 73/61.75

(58) Field of Classification Search
USPC ............................................ 73/570.5, 61.75
See application file for complete search history.

(56) References Cited

U.S. PATENT DOCUMENTS

| | | | |
|---|---|---|---|
| 5,633,552 A | 5/1997 | Lee et al. | |
| 6,168,948 B1 * | 1/2001 | Anderson et al. | 435/287.2 |
| 6,537,498 B1 | 3/2003 | Lewis et al. | |
| 7,601,287 B2 | 10/2009 | Haake et al. | |
| 2001/0055529 A1 * | 12/2001 | Wixforth | 417/53 |
| 2004/0069717 A1 | 4/2004 | Laurell et al. | |
| 2005/0241935 A1 | 11/2005 | Lewis et al. | |
| 2008/0229831 A1 | 9/2008 | Serban et al. | |
| 2008/0245745 A1 | 10/2008 | Ward et al. | |
| 2008/0302732 A1 | 12/2008 | Soh et al. | |

(Continued)

FOREIGN PATENT DOCUMENTS

| | | | |
|---|---|---|---|
| WO | WO 2007128045 A1 * | 11/2007 | |
| WO | WO-2007128046 A1 | 11/2007 | |
| WO | WO-2008083138 A1 | 7/2008 | |
| WO | WO-2008118740 A2 | 10/2008 | |

OTHER PUBLICATIONS

Nilsson, et al., Acoustic control of suspended particles in micro fluidic chips, Lab on a Chip, 4:131-135, 2004.

(Continued)

Primary Examiner — Peter Macchiarolo
Assistant Examiner — Rose M Miller
(74) Attorney, Agent, or Firm — Gifford, Krass, Sprinkle, Anderson & Citkowski, P.C.

(57) ABSTRACT

Examples of the present invention include apparatus and methods for particle focusing, for particles within a fluid sample. An example apparatus, which may be a microfluidic device, comprises a substrate, a channel receiving the fluid sample, and at least one surface acoustic wave (SAW) generator. The SAW generator may comprise electrodes supported by the substrate. In some examples, the channel has a particle focusing region located near a region of the substrate surface in which a SAW is generated. Particles are concentrated within one or more particle focus regions of the sample flow (the particle focus regions being appreciably narrower than the channel dimensions) by the effects of the SAW. As an example, a pair of SAW generators can be used to generate a standing surface acoustic wave (SSAW) that is used for particle focusing.

20 Claims, 10 Drawing Sheets

(56) References Cited

U.S. PATENT DOCUMENTS

| | | |
|---|---|---|
| 2009/0066936 A1 | 3/2009 | Huang et al. |
| 2009/0158823 A1 | 6/2009 | Kaduchak et al. |
| 2009/0162887 A1 | 6/2009 | Kaduchak et al. |
| 2009/0226994 A1 | 9/2009 | Lemor et al. |
| 2010/0200092 A1* | 8/2010 | Beltram et al. ............... 137/828 |
| 2010/0304501 A1* | 12/2010 | Lee et al. ...................... 436/518 |

OTHER PUBLICATIONS

Wang, et al., Single-molecule tracing on a fluidic microchip for quantitative detection of low-abundance nucleic acids, Journal of the American Chemical Society, 127:5354-5359, 2005.

Wang, et al., Dielectrophoresis switching with vertical sidewall electrodes for microfluidic flow cytometry, Lab on a Chip, 7:1114-1120, 2007.

Wiklund, et al., Ultrasonic standing wave manipulation technology integrated into dielectrophoretic chip, Lab on a Chip, 6:1537-1544, 2006.

Shi, et al., Focusing microparticles in a microfluidic channel with standing surface acoustic waves (SSAW), Lab on a Chip, 8:221-223, 2008.

Shi, et al., Acoustic tweezers: patterning cells and microparticles using standing surface acoustic waves (SSAW), Lab on a Chip, 9:2890-2895, 2009.

Mao, et al., Focusing fluids and light: enabling technologies for single-particles detection in the micro/nanoscale, IEEE Nanotechnology Magazine, 2:22-27, 2008.

Mao, et al., "Microfluidic drifting"—implementing three-dimensional hydrodynamic focusing with a single-layer planar microfluidic device, Lab on a Chip, 7:1260-1262, 2007.

Mao, et al., Single-layer planar on-chip flow cytometer using microfluidic drifting based three-dimensional (3D) hydrodynamic focusing, Lab on a Chip, 9:1583-1589, 2009.

Wood, C.D. et al., "Alignment of particles in microfluidic systems using standing surface acoustic waves," Applied Physics Letters, 2008, vol. 92, 044104 (Published online Jan. 30, 2008).

* cited by examiner

PARTICLE FOCUSING WITHIN A MICROFLUIDIC DEVICE USING SURFACE ACOUSTIC WAVES

CROSS-REFERENCE TO RELATED APPLICATION

This application claims priority to U.S. Provisional Application Ser. No. 61/200,958, filed Dec. 5, 2008, the entire content of which is incorporated herein by reference.

GRANT REFERENCE

This invention was made with government support under a grant NIRT-ECCS-0609128 awarded by the National Science Foundation (NSF). The government has certain rights in the invention.

FIELD OF THE INVENTION

The invention relates to methods and apparatus for particle focusing and particle characterization.

BACKGROUND OF THE INVENTION

Conventional particle focusing methods are used to spatially compress a sample flow of particles, typically in two dimensions. Improved methods and apparatus for particle focusing would be useful for numerous applications.

SUMMARY OF THE INVENTION

An example apparatus for focusing particles within a fluid sample comprises a substrate, one or more transducers for generating a surface acoustic wave (SAW) in the substrate, and a channel configured to receive a fluid sample including one or more species of particle. The fluid sample may be a sample fluid flow, and the sample fluid flow may have a focused particle stream after passing through the particle focusing portion of the channel.

A channel has a particle focusing portion where the channel is proximate a SAW region of the substrate, for example extending over the SAW region. The SAW region can be defined using a patterned material on the substrate. The channel may be provided by a formed element, such as a molded polymer formed element, adjacent the substrate. The particle focusing portion of the channel provides particle focusing within the fluid sample when a standing surface acoustic wave is generated. The fluid sample may comprise particles suspended in a liquid, such as an aqueous medium.

In some examples, the substrate is a piezoelectric substrate, and the SAW is generated using a transducer supported by the substrate. A standing surface acoustic wave (SSAW) may be generated using a pair of surface acoustic wave generators (SAW generators), which may each be an interdigitated transducer (IDT). The SSAW generators may be spaced apart on the substrate, and the SSAW region of the substrate is located where SAWs interact on the surface. In some examples, a pair of SAW generators is used, and the particle focusing region of the channel is located between the SAW generators, e.g. mechanically coupled to a SSAW region of the substrate so that the SSAW generates pressure forces within the fluid sample.

Example apparatus include microfluidic devices, the channel being a microchannel having at least one cross-sectional dimension (such as width or height) less than 1 mm, for example between 1 micron and 500 microns, and the particles may be microparticles such as cells, biomolecules, polymer beads, and the like.

An apparatus, as illustrated in FIG. 9, may be a particle characterization apparatus 400 further including a particle characterization device 404, the particle characterization device 404 characterizing the focused particles from the inventive particle focusing device 402. Particle characterization may include counting, sorting, detecting (including selective detection of one or more particle species), or otherwise characterizing particles. A particle characterization apparatus may include a radiation source providing a radiation beam incident on the focused particles, and/or a sensor receiving radiation scattered or otherwise obtained from the particles. Example particle characterization apparatus include a cytometer (such as a flow cytometer), fluorescence particle detector, fluorescence spectrometer, fluorescence-activated particle sorter, other particle sorter, particle counter, fluorescent spectrometer, or genetic analyzer. Particles may be cells (e.g. human cells), biomolecules, other bioparticles, or any other type of particle of interest.

An example method of focusing particles within a fluid sample including the particles comprises introducing the fluid sample to a channel proximate a substrate, and generating a surface acoustic wave (SAW) on the substrate. A SAW is an acoustic wave propagating along the surface of the substrate, and the surface may also be in contact with a fluid sample. The term acoustic does not limit the frequency of the SAW, which may greater than 1 GHz. Focused particles may be particles within a region of enhanced particle concentration within a liquid.

The SAW (such as a SSAW) induces pressure forces within the fluid so as to focus the particles within the fluid sample. The sample flow may be directed along a flow channel, the flow channel being supported by the substrate in which the SSAW is generated. A SSAW may be used to obtain three-dimensional focusing of the particles within the sample flow, the particles being focused in directions both parallel and normal to the substrate.

A novel on-chip micro/nano particle focusing technique was developed using surface acoustic waves (SAW), in particular using standing surface acoustic waves (SSAW). Example methods and apparatus are efficient, simple, fast, dilution-free, and applicable to virtually any type of particle, including both charged and uncharged microparticles. Example methods can be used with flow cytometry, cell sorting/counting, on-chip cell manipulation, tissue engineering, regenerative medicine, and many other applications.

An example apparatus, such as a microfluidic device, receives a sample flow including particles. The apparatus comprises a substrate, a channel (such as a flow channel) into which the sample is introduced, and one or more surface acoustic wave (SAW) generators. A SAW generator may be an interdigitated transducer (IDT, sometimes termed an inter-digital transducer) comprising interdigitated comb-shaped electrodes on a piezoelectric substrate. The channel may pass between a pair of IDTs. The IDTs and channel may both be supported by the same piezoelectric substrate. The SAW generators may be operated to produce a SSAW in a portion of the substrate proximate (possibly immediately adjacent to) the focusing portion of the flow channel. For example, a flow channel may be supported by the substrate, e.g. formed by a structure comprising a polymer or other material bonded to the substrate.

The flow channel has a particle focusing region located on a portion of the substrate in which the SAW exists. For example, flow channel may pass over a portion of the substrate having surface acoustic wave (SAW), the particles being focused within the flow channel by the effects of the SAW. The SAW may be a standing surface acoustic wave (SSAW). The substrate may be a generally planar substrate, for example a ferroelectric and/or piezoelectric substrate. A surface acoustic wave generator may comprise interdigitated electrodes supported by a ferroelectric or piezoelectric substrate. Two or more SAW generators may be used to generate an SSAW in the substrate, e.g. using interference effects between SAWs.

A method of focusing particles within a sample, which may be a method of three-dimensional particle focusing, includes producing a standing surface acoustic wave (SSAW), pressure waves within the sample generated as a result of the SSAW producing particle focusing. The sample may be a sample flow moving through a channel, the channel having a particle focusing region over a portion of the substrate in which the SSAW exists.

An apparatus for three-dimensional particle focusing of particles within a fluid sample comprises a substrate having a substrate surface, a surface acoustic wave generator, operable to generate a surface acoustic wave (SAW, such as a SSAW) within a SAW region of the substrate surface, a channel configured to receive the fluid sample, the channel having a particle focusing portion proximate the SAW region of the substrate, the particle focusing portion providing focused particles within the fluid sample when the SAW is generated. The substrate surface may form a wall of the channel, and the SAW region of the substrate may form a wall of the particle focusing portion of the channel.

DETAILED DESCRIPTION OF THE INVENTION

Figure 1:
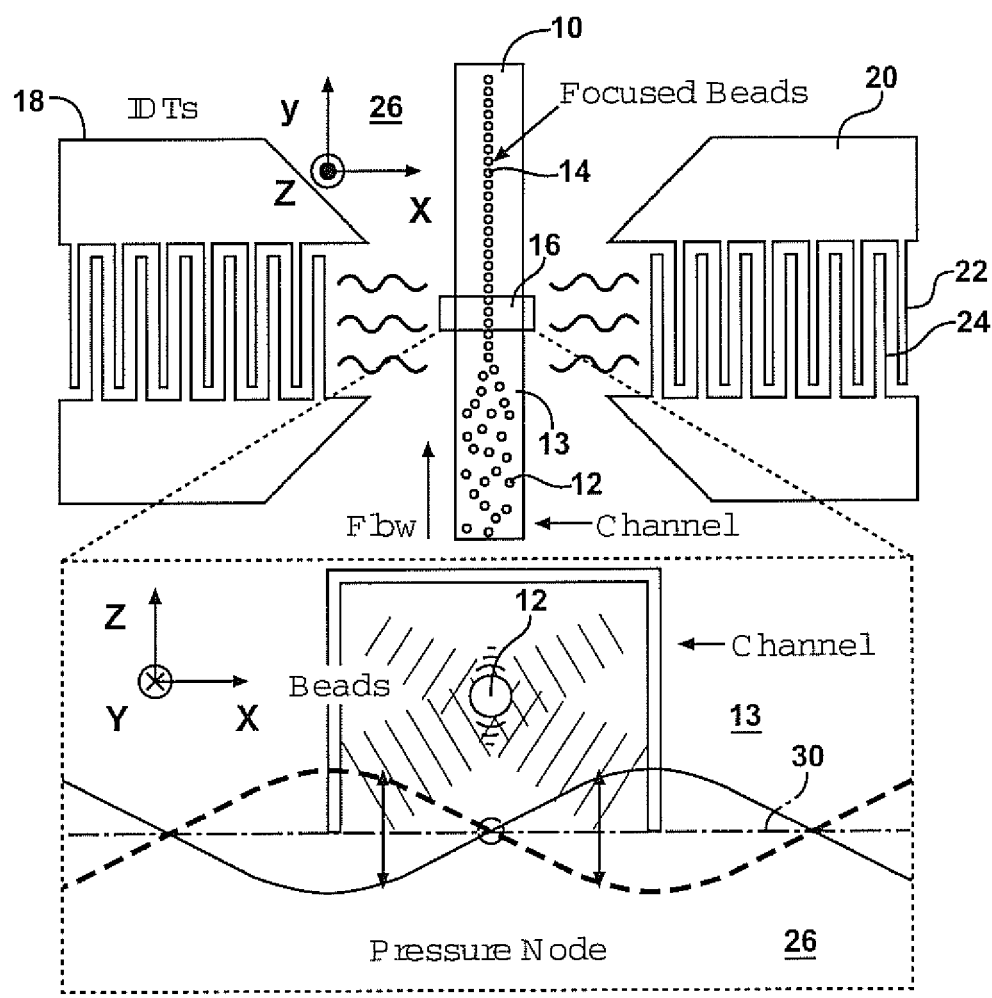
FIG. 1 is a schematic of the SSAW focusing device, illustrating its working mechanism, also illustrating the SSAW pressure field inside the channel, where the particles are focused at the pressure node.

Example apparatus and methods using a novel acoustic manipulation technique using surface acoustic waves (SAW), in particular standing surface acoustic waves (SSAW), allow fast and effective particle focusing. Examples include apparatus and methods for microparticle focusing inside a microfluidic channel. Example approaches are simple, fast, dilution-free, and can be used to focus virtually any microparticles, including both charged and uncharged particles. The transparency of the focusing device makes it compatible with most optical characterization tools used in biology and medicine, allowing particle characterization by fluorescence and/or other optical techniques. A surface acoustic wave (such as a SSAW) can be used for manipulation of arbitrary particles, such as micro/nano particles, for example particle focusing within a fluid flow.

A SSAW-based technique localizes most of the acoustic energy on the surface of the substrate, and has little loss along the propagation line, lowering the power consumption and improving the uniformity of the standing waves. The SSAW technique is compatible with standard soft lithography techniques, and can be used in a wide variety of on-chip biological/biochemical applications. In experimental examples, a standing surface acoustic wave (SSAW) focusing technique was used with a microfluidic device using a PDMS channel fabricated by standard soft lithography.

Manipulation and focusing of micro/nanoparticles was achieved using surface acoustic waves (SAWs) generated on a piezoelectric substrate. The leakage of SAWs through the surface results in pressure gradients in the liquid, and these gradients can be used to manipulate suspended particles. Acoustic particle manipulation does not depend on the charge or polarity of the particles. As such, the method can be applied to virtually any type of particles.

An example device includes a pair of interdigital transducers (IDTs, also referred to as interdigitated transducers) supported by a piezoelectric substrate. An EDT may comprise two interlocking comb-shaped electrodes, the electrodes being provided by a metal or other conducting coatings supported by the substrate. The piezoelectric substrate may comprise a ferroelectric material such as lithium niobate, and the IDTs may be deposited on a lithium niobate substrate.

Particle suspensions (such as microparticle and/or nanoparticle suspensions) are introduced through a channel located between two IDTs. The channel may be formed in a polymer, such as PDMS. For example, the channel may be formed by a molded polymer element on the substrate, and may be a microchannel. The molded polymer element may additionally include a cut-out (area in which it does not contact the substrate) so as to define the SSAW region of the substrate. A radio-frequency signal is applied to each IDT, which then generates a SAW that propagates toward the channel. The interference of the SAWs results in the formation of a SSAW on the substrate.

With fluids filling the channel, the SSAW leaks into the liquid medium and induces pressure waves in the medium. Such pressure waves are also standing waves because of the periodic distribution of their pressure nodes (minimum pressure amplitude) and anti-nodes (maximum pressure amplitude). Pressure wave periods are determined by their origin, in this example the SSAW on the piezoelectric substrate. These pressure waves result in acoustic radiation forces that act on the particles, forcing them to move toward either the pressure nodes or antinodes. A channel can be designed in such a way that only one pressure node (or antinode) is located within the center of the channel. As a result, the particles in a representative experimental example were focused toward the channel center while they traveled along with the fluid flow. However, other configurations are possible.

As a fluid flow approached a SSAW propagation area, particles at outside the propagation area do not experience acoustic forces and may be distributed uniformly across the width of the channel. As the particles enter the SSAW propagation area, they experience acoustic forces and begin to migrate toward the center of the channel, which corresponds to the focusing process. Well stabilized focused streams can be obtained, and stream widths of less than 10 µm can be obtained, for example approximately 5 µm. Stream widths may be less than three times the diameter of a single particle, 5% of the SSAW wavelength, and less than 20% (e.g. 10% or less) of the channel width. Particles remain focused even after flows move outside the SSAW propagation area, due to the laminar nature of the flow.

FIG. 1 shows a schematic of a SSAW focusing device comprising a pair of interdigital transducers (IDTs) deposited on a piezoelectric substrate, and a PDMS-based channel, in this example a microfluidic channel, bonded with the substrate and positioned between the two IDTs.

The figure shows the channel 10 receiving a flow of suspended particles (12) within a fluid medium 13. As illustrated, the flow is upwards, as indicated by an arrow. The channel passes between a pair of IDTs (18 and 20 respectively) supported by a substrate, the IDTs generating a SSAW in the supporting substrate. For illustrative simplicity, the figure does not show the channel walls. A particle focusing region is formed where the channel passes through the SSAW propagation area, and this focuses the particles to a narrow particle stream 14 within the center of the channel 10.

The figure also illustrates the SSAW pressure field inside the channel, where the particles are focused at the pressure node. In this example, the channel width is designed to cover only one pressure node such that particles (in this example, polymer beads) are focused at that node when the SSAW is generated. The SSAW is illustrated by the solid and dashed undulating lines, representing (not to scale) the standing surface wave in the surface of the substrate 26. If the IDTs are not operating, the substrate surface would be planar (shown as line 30), and there are no particle focusing forces within the fluid medium. The figure shows a particle such as 12 being urged to the center of the channel by pressures within the fluid medium 13, induced by the SSAW in the substrate surface 30. In this example, the particles tend to collect above a pressure node on the surface.

Microparticle solutions can be infused into the microfluidic channel by a pressure-driven flow, for example using a pump. Once an RF signal is applied to both IDTs, two series of surface acoustic waves (SAW) propagate in opposite directions toward the fluid sample (a particle suspension solution) inside the channel. The constructive interference of the two SAW results in the formation of a SSAW, as well as the periodic distribution of the pressure nodes and anti-nodes on the substrate (regions of minimum and maximum pressure amplitude, respectively).

When the SSAW encounter the fluid sample inside the channel, leakage pressure waves in a longitudinal mode are generated, causing pressure fluctuations in the medium. These pressure fluctuations result in acoustic radiation forces that act laterally (in the x-direction of FIG. 1) on the particles. As a result, the suspended particles inside the channel are forced toward either the pressure nodes or antinodes, depending on the density and compressibility of the particles and the medium. When the channel width covers only one pressure node (or antinode), the particles are trapped in that node and consequently, particle focusing is achieved.

A pressure node (or antinode) may be centered laterally within the channel to obtain a centralized particle focus within the channel.

Figure 2:
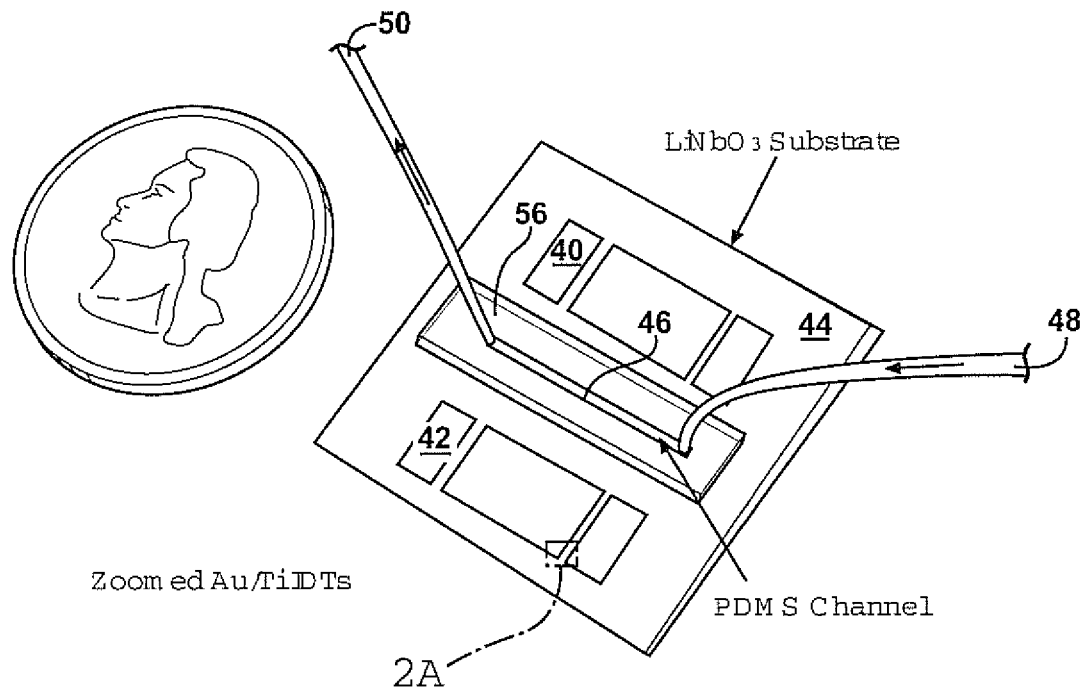
FIG. 2 shows a bonded SSAW focusing device comprising a LiNbO$_3$ substrate with two parallel IDTs and a PDMS (polydimethylsiloxane) channel, including an inset (2A) showing a zoomed-in region of an IDT electrode.
Figure 2A:
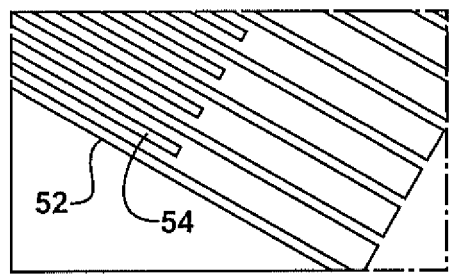

FIG. 2 is derived from a photograph of an example device used to obtain particle focusing. The bonded SSAW focusing device illustrated in FIG. 2 comprised a lithium niobate ($LiNbO_3$) substrate 44 with a pair of spaced apart parallel IDTs and a channel 46 extending between the IDTs formed in PDMS (56). The IDTs include electrode pads such as 40 and 42 at each end, with approximately rectangular regions of interdigitated stripe electrodes between them. The inset (FIG. 2A) shows more details of the interdigitated electrodes 52 and 54 for one of the IDTs. The channel has inlet 48 and outlet 50, in fluid communication with the channel. A U.S. quarter is shown on the left hand side for size scale.

In this example, the substrate was a Y+128° X-propagation $LiNbO_3$ piezoelectric wafer, 500 µm thick, which was chosen as the substrate due to its high coupling coefficient in SAW generation. The two IDTs were arranged parallel to each other, and were formed by e-beam evaporation of Ti (50 Å, adhesive layer) and Au (800 Å). The period of the IDTs was 100 µm, and each IDT electrode was 9 mm long and 25 µm wide.

The side walls and upper wall of the channel are provided by PDMS (56), and the base of the channel is provided by the substrate. This PDMS microchannel had both a width and depth of 50 µm and a length of 1.3 cm, and was bonded to the $LiNbO_3$ substrate and aligned between the two IDTs.

Smooth side openings (cut-outs) aligned on either side of the PDMS channel were used to more precisely define the working region of the SSAW, and reduce the propagation loss.

The bonded device was mounted on the stage of an inverted microscope (Nikon TE2000U). A solution ($1.176 \times 10^7$ beads/ml) of fluorescent (Dragon Green) polystyrene particles (diameter 1.9 µm, Bangs Laboratories) was injected into the channel using a syringe pump (KDS210, KD Scientific). An AC signal generated by an RF signal generator (Agilent E4422B) was amplified with a power amplifier (Amplifier Research 100A250A). This signal was split into two coherent signals, which were subsequently applied to the two DTs to generate SSAW. The signal frequency was set to be 38.2 MHz (resonance frequency) and the applied power was 24 dBm (~250 mW).

Figure 3A:
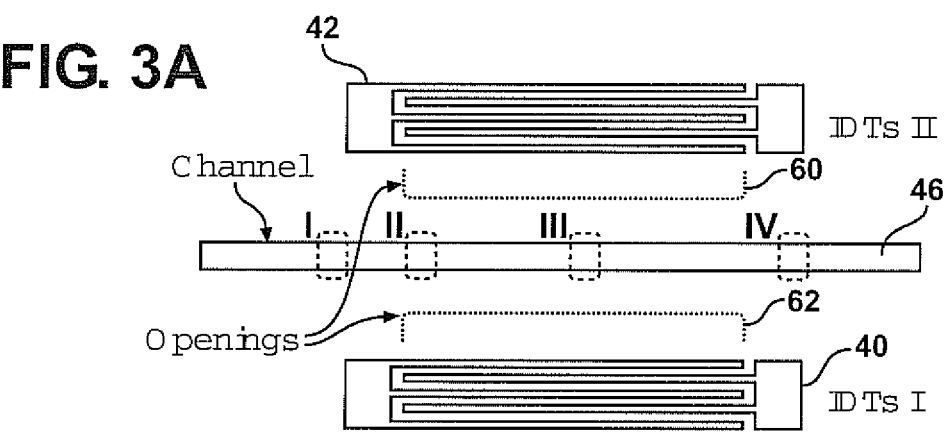
FIG. 3A is a schematic which indicates the positions of the chosen sites (I-IV) for monitoring the focusing effects.

FIG. 3A is a simplified schematic of the device of FIG. 2, showing channel 46 extending between the IDTs 40 and 42. For illustrative simplicity, the schematic does not show all the interdigitated electrode stripes such as 52 and 54, shown in the inset of FIG. 2, within the IDTs. FIG. 3A also indicates the positions of four chosen sites (11V) for monitoring the focusing effects.

FIGS. 3B-3E are illustrations derived from recorded fluorescent images at the four sites (I-IV), respectively. The distribution of fluorescent microparticles was recorded during the focusing process at the regions marked as I, II, III and IV in FIG. 3A. The 10 micron scale bar (not shown) is approximately a quarter inch long. Further photographic details are found in Jinjie Shi, et al., "Focusing Microparticles in a Microfluidic Channel with Standing Surface Acoustic Waves (SSAW)", *Lab on a Chip*, Vol. 8, pp. 221-223, (2008).

Figure 3B:
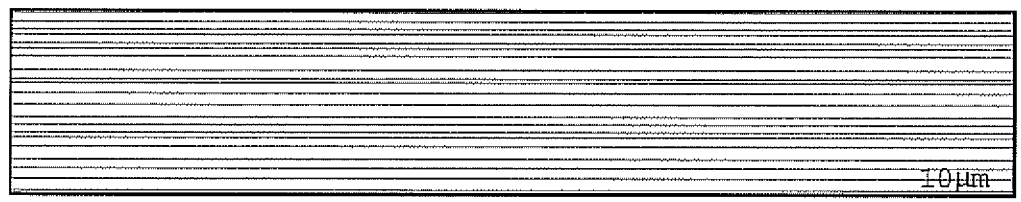
FIGS. 3B-3E show represent fluorescent images collected at sites (I-IV), respectively.

FIG. 3B, obtained at site I, was not within the SSAW propagation area and so microparticles barely experienced acoustic forces in this region. As a result, the distribution of microparticles in this region was uniform across the width of the channel.

Figure 3C:
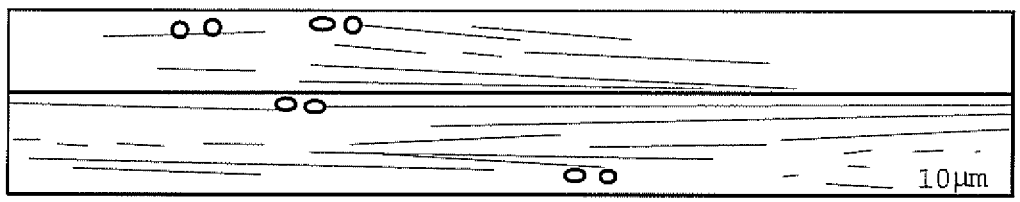

FIG. 3C shows that as particles entered the area in which the SSAW propagated (site II), the acoustic force exerted on the particles drove the particles toward the center of the channel (where pressure nodes existed). As the particles exited Site II, they were focused into a narrow stream in the middle of the channel. Based on the flow velocity (6.7 cm·s$^{-1}$) and the distance (~300 μm) over which the particles traveled from the unfocused site to the totally focused site, the duration of the focusing process was calculated to be 4.5 ms.

Figure 3D:

FIG. 3D shows that at site III, the focused stream was well-stabilized, and the width of the stream was measured to be approximately 5 μm, less than three times the diameter of a single particle, 5% of the SSAW wavelength, and 10% of the channel width.

Figure 3E:
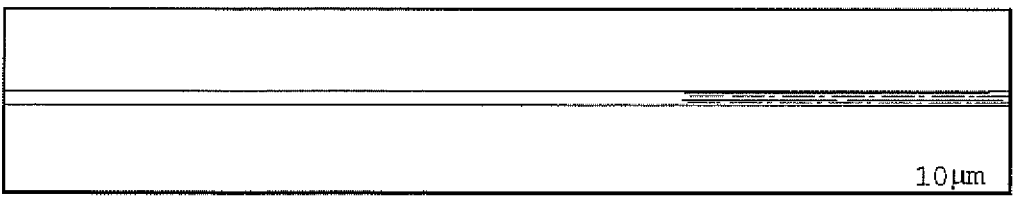

FIG. 3E shows the particle distribution at Site IV where SSAW did not propagate, and the width of the focusing stream remained constant. This phenomenon was due to the laminar nature of the flow.

Figure 4A:
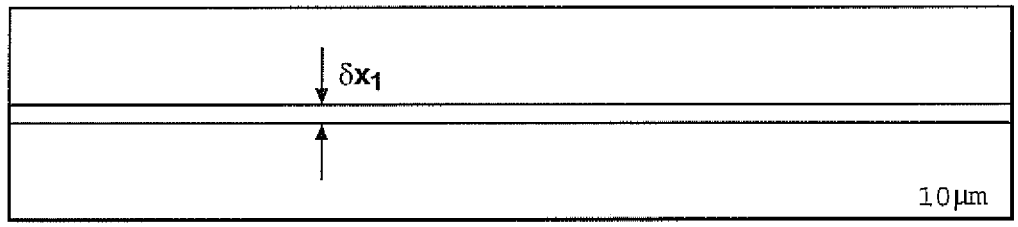
FIGS. 4A and 4B show representations of experimental data for the focusing performance at a working frequency of 38.2 MHz (corresponding to $\lambda_1=100$ μm) and 19.116 MHz (corresponding to $\lambda_2=200$ μm), respectively.
Figure 4B:
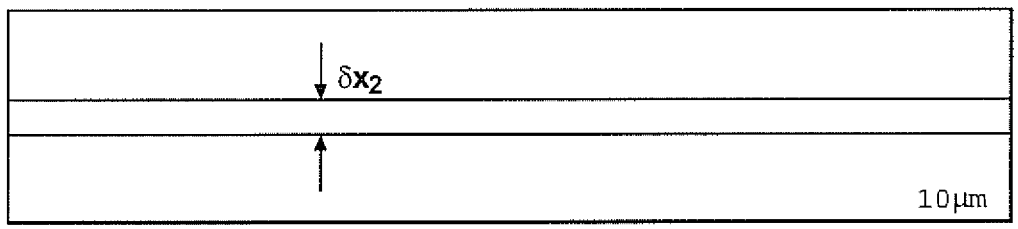

FIGS. 4A and 4B depict the experimental results monitored from two devices driven at the same power (25 dBm) but different wavelengths ($\lambda_1$=100 μm and $\lambda_2$=200 μm, respectively). The SSAW focusing effect was dependent upon the frequency of the acoustic waves. The measured focusing width $\delta x_2$ (~10 μm, FIG. 4B) for device II was about two times greater than $\delta x_1$ (~5 μm, FIG. 4A). This observation was due to the balance of acoustic radiation forces and acoustic interparticle forces (e.g., Bjerknes forces, van der Waals force, electrostatic forces), which originate from the acoustic oscillation between particles in the focusing band. When such particles are driven close to each other toward the pressure node by the acoustic radiation forces, the overall effects of the interparticle forces become repulsive to balance the acoustic radiation force.

Figure 4C:
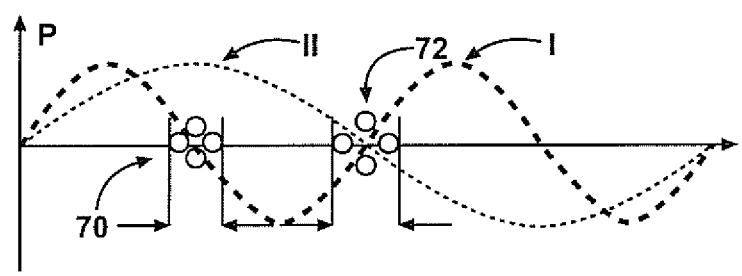
FIG. 4C is a qualitative analysis (not to scale) of the particle concentration at pressure nodes at two different working, frequencies.
Figure 4D:
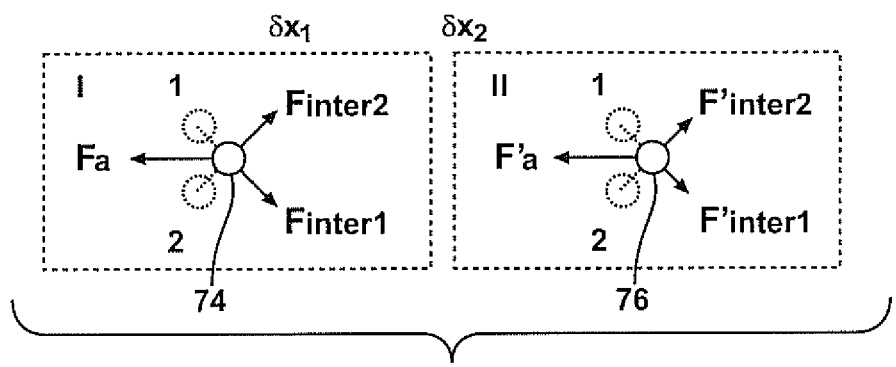

FIG. 4C shows the pressure field and force balance diagram for the particles in devices I and II. These particles were exposed to acoustic waves with identical pressure amplitude but different wavelengths ($\lambda_2$=2$\lambda_1$), as illustrated by the dashed lines labelled "I" and "II". Since the acoustic radiation force $F_a$ exerted on a particle is inversely proportional to the acoustic wavelength, the acoustic radiation force exerted on particles in device I was twice the force on those in device II. This higher acoustic radiation force was balanced by a larger repulsive force between particles. Therefore, as shown in the inset boxes, the repulsive force packed the particles (74) closer in device I (FIG. 4A) compared with the particles (76) in device II (FIG. 4B), thereby causing a narrower focusing width in the former device.

Sub-micrometer focusing widths can be achieved as increasing the working frequency is increased. This frequency-dependent characteristic presents another advantage of SAW over BAW: it is relatively easy to fabricate IDTs with smaller periods and generate higher-frequency (hundreds of MHz) SAW, while the frequencies for most of the current BAW-based particle manipulating techniques are 1-2 MHz.

Figure 5A:
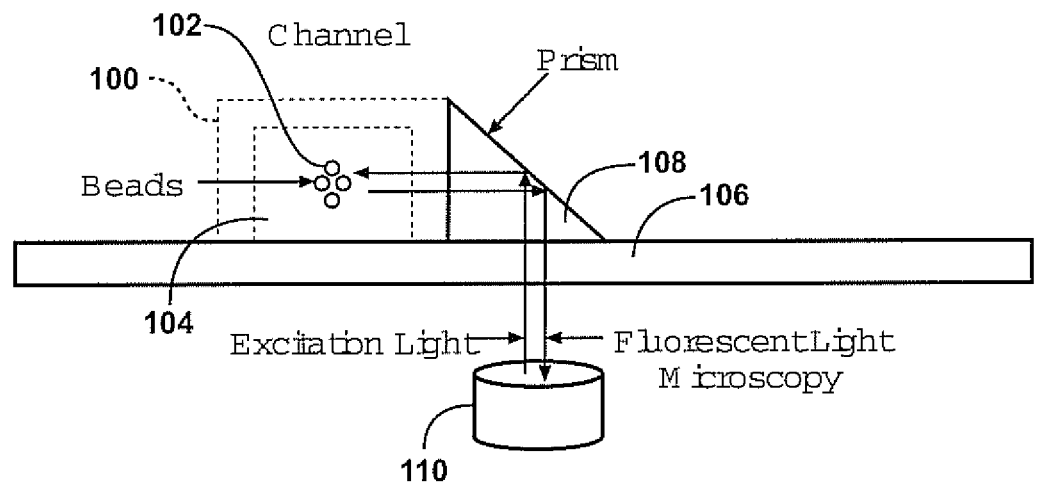
FIG. 5A shows a 45° prism is placed along the sidewall of the channel in order to characterize the particle distribution inside the microfluidic channel.

FIG. 5A shows a simplified schematic for characterizing the particle distribution inside the microfluidic channel in a direction normal to the substrate. The configuration includes channel 100, including particles 102 in fluid medium 104, substrate 106, prism 108, and fluorescence microscope 110. The 45° prism 108 is placed along the sidewall of the channel 100, which bends the excitation light from the fluorescence microscope to a lateral direction (parallel to the substrate) and shines on the fluorescent particles inside the channel. The generated fluorescent light from the particles is then be bent downwards by the prism and sensed by microscopy. In this way, the particle distribution in the vertical direction in the channel can easily be monitored without using expensive equipment like confocal microscopy.

Figure 5B:
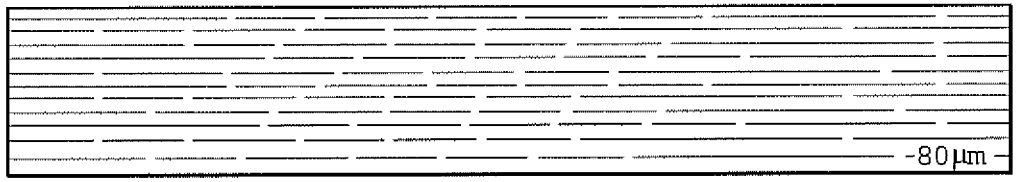
FIG. 5B represents particle distribution inside the channel when SSAW is off.
Figure 5C:
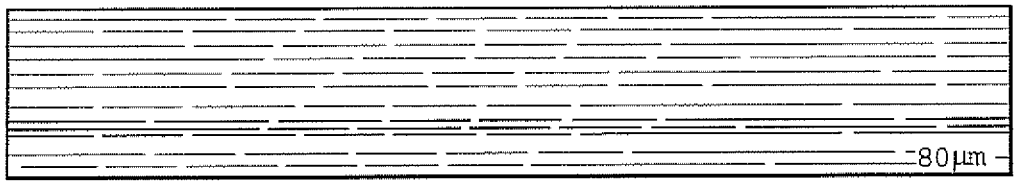
FIG. 5C represents particle focusing in the vertical direction when the SSAW is generated.

FIG. 5B shows the particle distribution inside the channel when SSAW is off. The particles are uniformly distributed in a vertical direction (normal to the substrate). The 80 micron scale bar (not shown) is approximately 1 cm long. FIG. 5C shows particle focusing occurring in the vertical direction when SSAW is turned on. These results show that SSAW can be used for 3D focusing of particle flows, as particle focusing occurs in planes both normal and parallel to the substrate.

Hence, SAWs, such as a SSAW, can be used for both 2D and 3D particle focusing. Three-dimensional particle focusing (particles concentrated in orthogonal planes, parallel and perpendicular to the substrate) was achieved without any additional flows, such as sheath flows. In some examples, the sample fluid does not flow in the channel during focusing, and particle focusing can be controlled by the spatial distribution of pressure nodes and antinodes. In other example, particle flow allows focused particles to move away from the focusing region of the channel. In some examples, a propagating SAW can be used to move or otherwise spatially control particles within a fluid sample.

The method of FIG. 5 allows the particle distribution in the vertical direction inside the channel to be easily characterized. Experiments with this configuration showed that the particles are not only focused in the lateral direction (parallel to the substrate), but also focused in the vertical direction (normal to the substrate), giving 3D focusing.

The techniques according to examples of the present invention can be used in various improved methods and apparatus (for example, flow cytometry, cell sorting/counting, tissue engineering, and the like).

Device Fabrication

Figure 6:
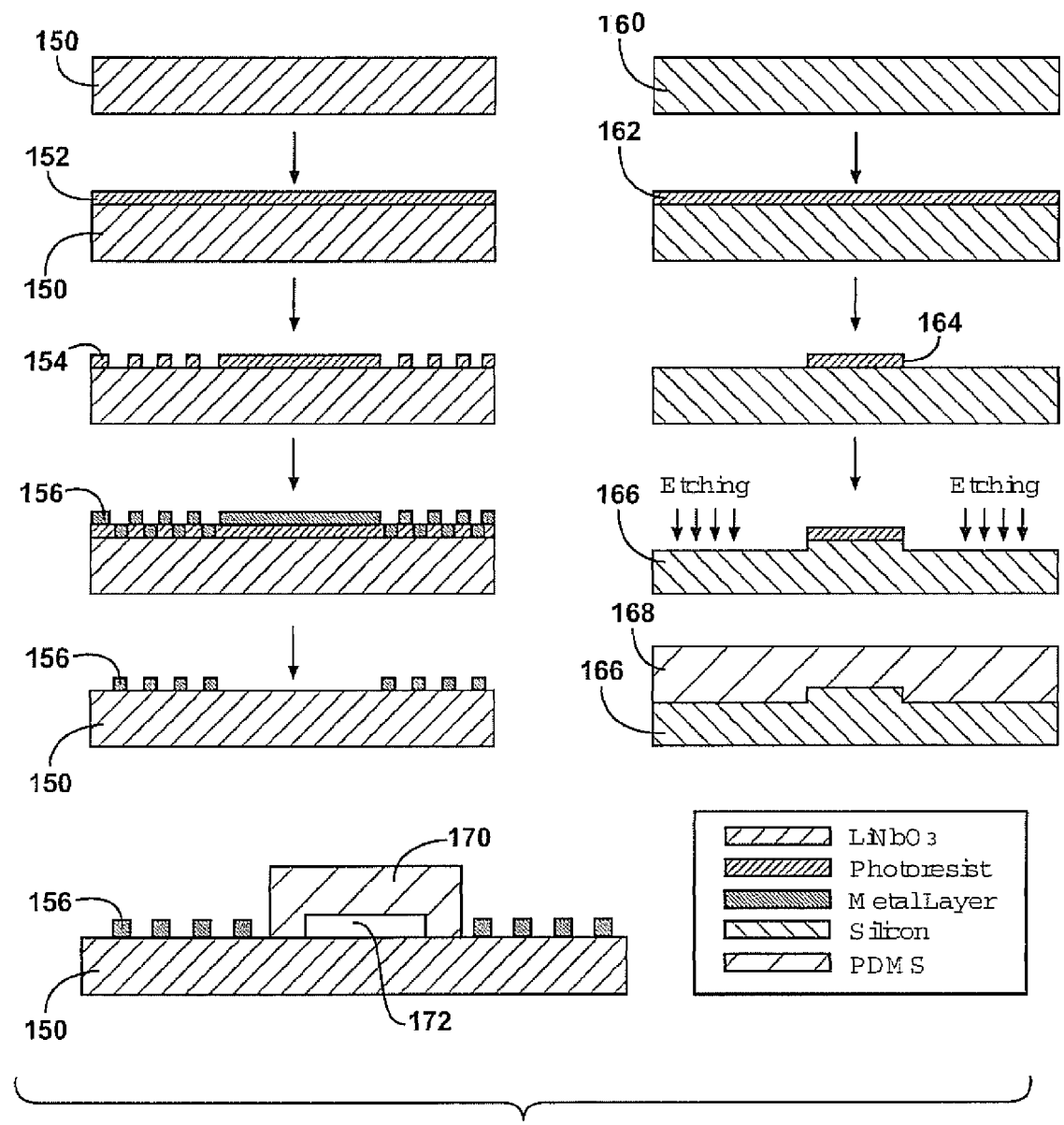
FIG. 6 shows an example device fabrication method.

FIG. 6 shows an example device fabrication process, which includes SAW substrate fabrication, PDMS microchannel fabrication, and the bonding of PDMS microchannel to the SAW substrate. Fabrication of an example device is described below in more detail. However, examples of the invention are not limited to this device configuration.

The figure shows the fabrication of the SAW substrate (left hand side of the figure), in which photoresist (152) is used to obtain a patterned metal electrode (156) on a substrate 150. The thin layer photoresist SPR3012 (MicroChem, Newton, Mass.) was spin-coated on a Y+128° X propagation lithium niobate (LiNbO$_3$) wafer, patterned using a UV light source and developed in photoresist developer (MF CD-26, Microposit). A double metal layer (Ti/Au, 50A/800A) was subsequently deposited on wafer using an e-beam evaporator (Semicore Corp), followed by a lift-off procedure (removing metal 154 deposited on the photoresist layer) to form the interdigitated electrodes (IDTs) to generate SAW.

The figure also shows the fabrication of the polydimethylsiloxane (PDMS) microchannel using standard soft-lithography and mold-replica technique (right hand side of the figure). The silicon mold 166 for the microchannel 170 was made by patterning a photoresist layer 162, and etching to produce a protrusion 164 from the silicon substrate 160, which gives the mold 166. The mold was then coated with PDMS, giving a trench in the PDMS that forms the channel 172 within the molded PDMS 170. Similar formed elements may be fabricated in other polymers (such as other silanes), gels, and other moldable materials. A formed element, including one or more trenches used for microchannel(s), may be transparent at particle characterization wavelengths of interest. The channel 170 has a generally rectangular profile, with PDMS as three sides, and the substrate as the base.

The silicon mold was formed by photoresist patterning (Shipley 1827, MicroChem, Newton, Mass.) and a subsequent Deep Reactive Ion Etching (DRIE, Adixen, Hingham, Mass.). The etch depth was set at 50 µm. In order to reduce surface energy and hence the damage to the PDMS channel during the demolding process, the silicon mold was coated with 1H,1H,2H,2H-perfluorooctyltrichlorosilane (Sigma Aldrich, St. Louis, Mo.) in a vacuum chamber after DRIN. Sylgard™ 184 Silicone Elastomer Base and Sylgard™ 184 Silicone Elastomer Curing Agent (Dow Corning, Midland, Mich.) were mixed at a 11:1 weight ratio, cast onto the silicon mold, and cured at room temperature overnight.

Once peeled from the silicon mold, inlets and outlets are created using a silicon carbide drill bit. Surfaces on both the PDMS substrate and the SAW device are activated with oxygen plasma (oxygen flow rate 50 sccm, chamber pressure 750 mTorr and power 150 W) to facilitate the bonding. In order to achieve precise alignment between the channel and the IDTs, four Ti/Au metal alignment markers were fabricated in the same fabrication process for the IDTs. The alignment marks were located between two parallel IDTs, corresponding to the four inner corners of the side openings parallel to the channel. The alignment of the SAW device and PDMS channel was conducted manually under the microscope. A drop of ethanol was placed on the surface of the SAW device as lubricant so that the PDMS channel could slide on top of SAW device until the alignment marks overlap the corresponding corners of the side openings.

After alignment, ethanol was removed by leaving the aligned device in a vacuum chamber with the temperature of 50° C. for 15 minutes. The entire bonding process was processed in a clean room to avoid the contamination the channel. Finally, polyethylene tubings (Becton Dickson, Franklin Lakes, N.J.) were inserted into the inlets to connect the device to a syringe pump (KDS 210, KD Scientific, Holliston, Mass.).

In order to obtain the working frequency, an AC signal with fixed input power but varying frequency was applied to one of the IDTs, and another IDT served as a receiver. When the output signal reached its maximum, the applied frequency was determined as the working frequency. Still images and a real-time video of beads focusing process were recorded using an inverted microscope (TE 2000U, Nikon, Melville, N.Y.) and a CCD camera (CoolSNAP HQ2, Photometrics, Tucson, Ariz.).

Real-time video monitoring showed fluorescent polystyrene beads focusing inside a microchannel. At monitoring site I (outside of the SSAW region, corresponding to the monitoring sites of FIG. 3A), the fluorescent beads were uniformly distributed through the entire channel. At monitoring position II (an edge of the SSAW region), beads began to be focused toward the center of the channel. At site III (center of the SSAW working area), the beads were focused in the center of the channel. At site IV (downstream, outside of the SSAW region of the substrate), and beads remained focused due to the laminar property of the flow. The illustrated beads are representative of various particle types.

In some experiments, microbeads were patterned in microfluidic channels using standing surface acoustic waves (SSAWs). A SSAW was formed using two parallel interdigital transducers (IDTs) on a $LiNbO_3$ substrate. A PDMS microchannel was aligned with the IDTs and bonded with the substrate. A solution of fluorescent polystyrene beads (diameter: 1.9 microns) was injected into the channel through a pressure driven flow. When a 25 dBm AC signal (frequency: 23.9 MHz) was applied to the IDTs, the beads were patterned into two straight lines (~5 microns in width) along the pressure nodes inside the channel.

There may be one or more pressure nodes within the channel. If SSAW is formed by counter-propagating SAWs, the pressure nodes may be elongated. However, other configurations of IDT are possible, allowing various configurations of pressure node to be obtained.

Figure 7:
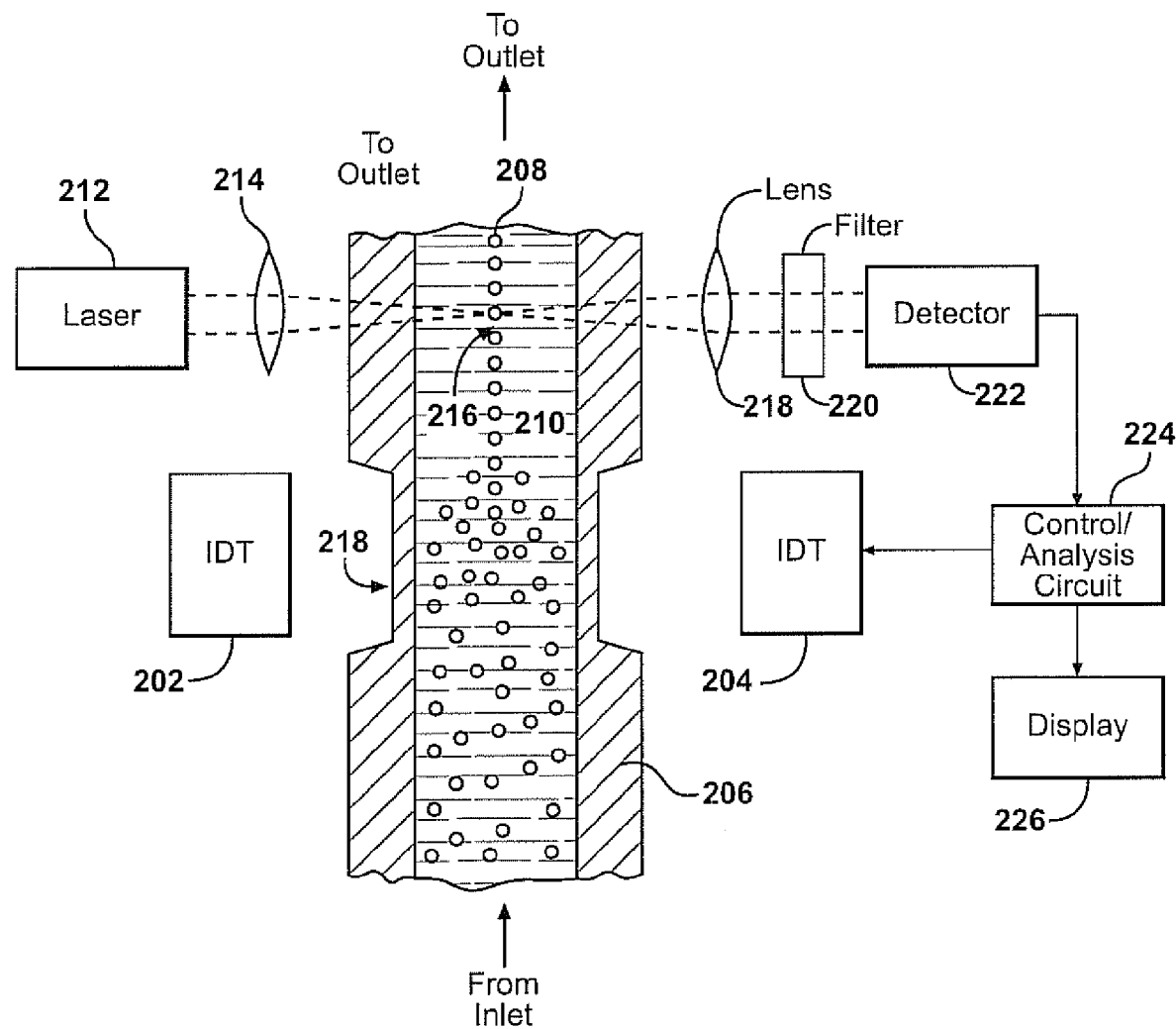
FIG. 7 shows a schematic of an example system.

FIG. 7 shows a simplified schematic of an example system, not to scale. The figure shows first and second transducers 202 and 204, in this example interdigital transducers (IDTs), channel 200 bounded by sidewalls 206 (shown in cross-section) including particles such as 208, radiation source (in this example laser 212), and incidence and collection lenses 214 and 218. The incidence lens focuses the incident radiation, in this case a laser beam, to focus 216. The collection lens collects detected radiation (which may be at the incidence radiation wavelength or other wavelength) and passes it to the detector 222.

An optional filter 220 can be used to reject unwanted wavelengths from the detector, for example passing fluorescence radiation and rejecting laser wavelengths. The sidewalls are shown with cut-outs 218 to facilitate SAW propagation. Sidewall cut-outs can also be used for incidence and/or detected radiation. An electronic circuit (control/analysis circuit 224) is used to provide appropriate drive signals to the transducers 202 and 204 (the former connection not shown for illustrative clarity), and receives detector signals. The electronic circuit may comprise a processor and other conventional associated components. A display 226 is used to show analysis.

For example, the apparatus of FIG. 7 may be a flow cytometer or other particle characterization apparatus. A plurality of radiation sources may be used, for example lasers at more than one wavelength. The figure shows detection at an angle of about zero degrees, relative to the incidence radiation wavevector, but other detection geometries can be used including orthogonal detection, which may be through the substrate or other wall of the channel.

Unlike a conventional flow cytometer, no additional fluid flow (such as a sheath flow) is needed to obtain particle focusing.

Figure 8A:
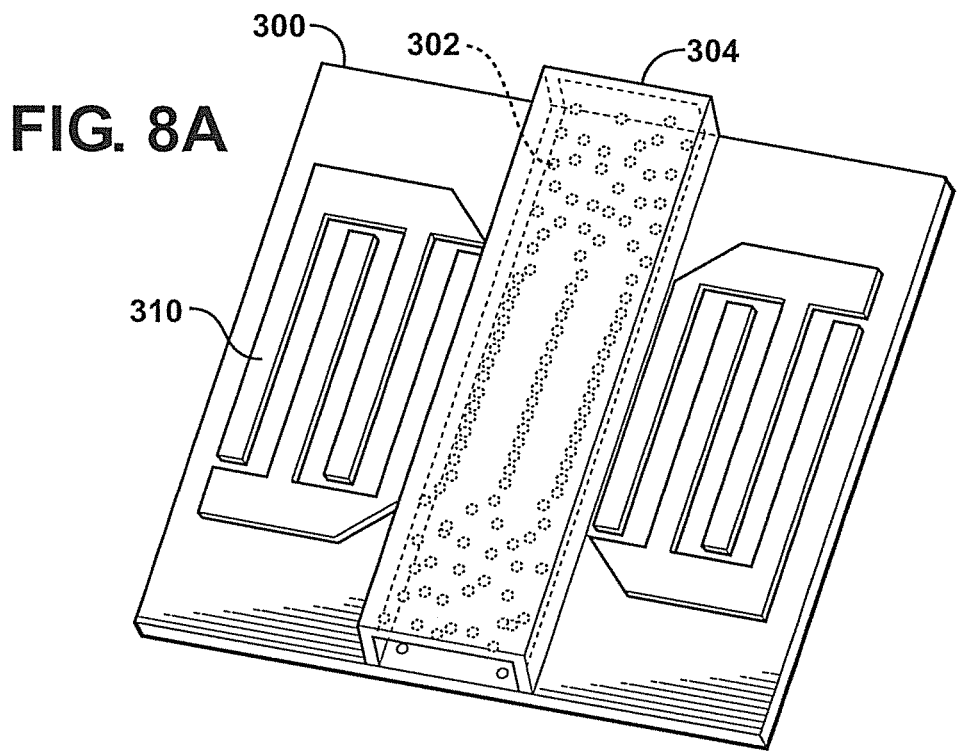
FIGS. 8A-8D illustrate surface acoustic waves in a substrate, and formation of pressure nodes, and FIG 9. illustrates a particle characterization apparatus.
Figure 8B:
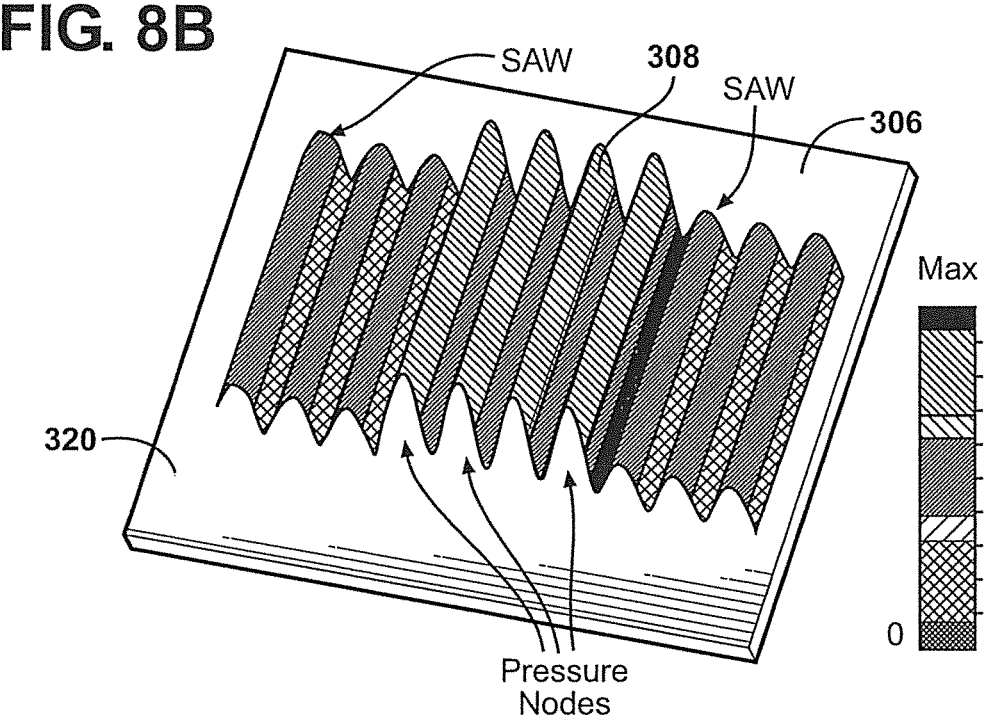

FIGS. 8A-8D illustrate simulations of surface acoustic waves in a substrate, and formation of pressure nodes. FIG. 8A shows an apparatus 300 comprising a pair of transducers (e.g. IDT at 310) in which particles within the channel 304 are focused into three particle focus streams by SSAW-induced pressure nodes. FIG. 8B shows the three pressure nodes 308 that are covered by the microfluidic channel 304. In such a configuration, there may (or may not) be sample flow within the channel. In this example, SAWs propagating in approximately opposite directions constructively interfere with each other to form the pressure nodes.

Figure 8C:
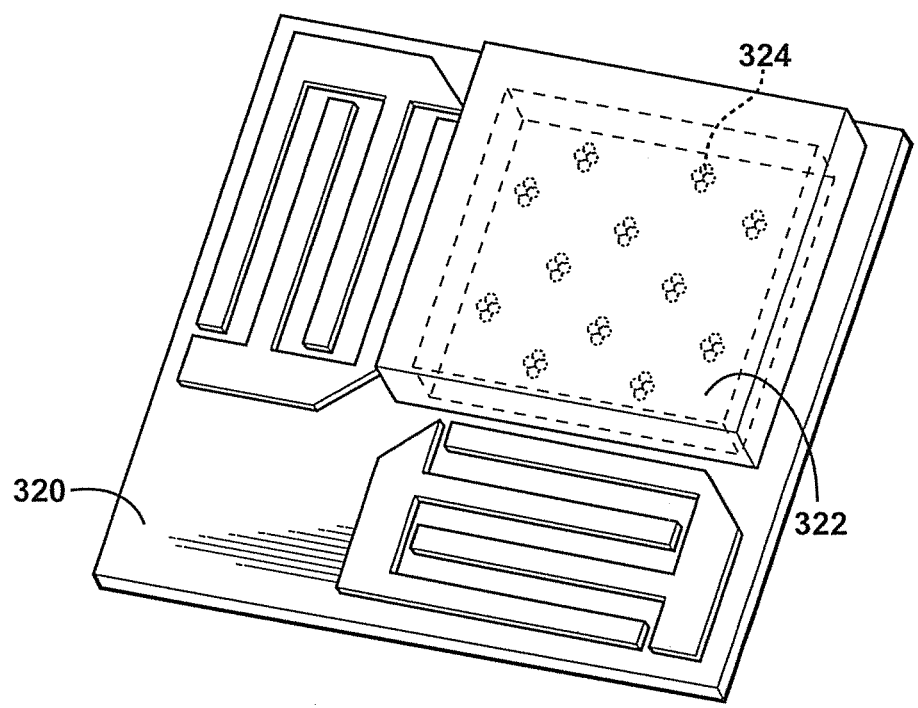
Figure 8D:
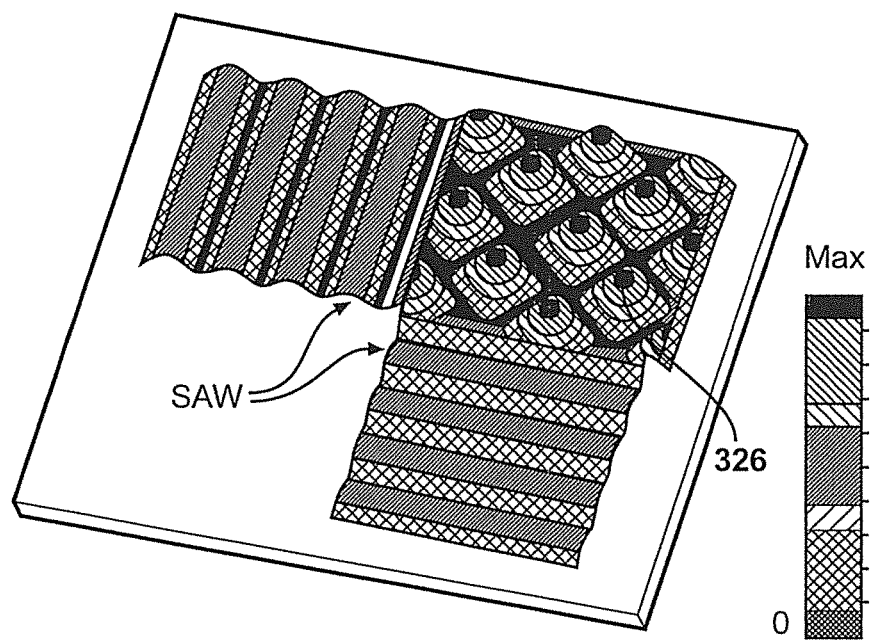
Figure 9:
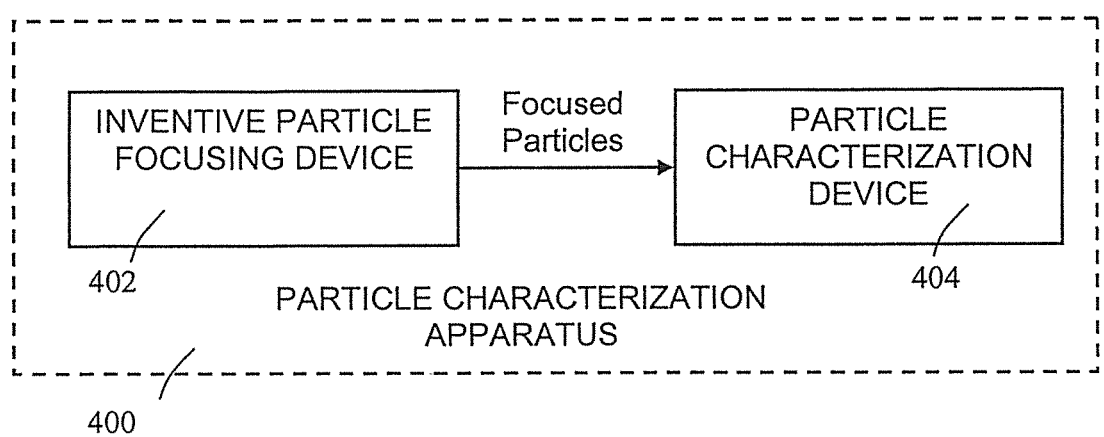

FIG. 8C shows another apparatus configuration 320 showing localized particle focusing (optionally without sample flow) at locations such as 324 within channel 322 using a pair of IDTs. In this example, the SAWs generated by each transducer propagate in generally orthogonal directions. The SAWs interact to form localized pressure nodes 326.

In other examples, SAWs generated by one or more transducers may propagate at any angle relative to each other, e.g. between zero and 90 degrees, to obtain desired pressure node patterns. Particles may be localized at pressure nodes or antinodes, depending on relative densities of particle and particle support medium, the pressure nodes (antinodes) resulting from constructive (or destructive) interference of propagating SAWs.

When f=0.02 GHz, the attenuation coefficient of SAW on $LiNbO_3$ was calculated to be $\alpha=1$ dB/m. The propagation of SAW excited by IDTs on a piezoelectric substrate was simulated as plane waves propagating with frequency-dependent attenuation. The acoustic pressure field was assumed to be uniform along the direction transverse to the wave propagation and can be expressed as $$p(x) = p_0 \cdot e^{-\alpha x/2} \cdot e^{Rk \cdot x - 2\pi f \cdot t})$$

where $p_0$, $\alpha$, k, and f are the original acoustic pressure amplitude, attenuation coefficient, wave vector, and operation frequency, respectively. Using input AC signal power P=200 mW, and a SAW working area A=$10^{-4}$ m$^2$, the acoustic pressure was calculated as $1.904 \cdot 10^5$ Pa. The frequency dependent attenuation coefficient of SAW on this piezoelectric substrate was determined as $\alpha=0.19f+0.881f^{1.9}$ with f being the SAW operational frequency in GHz.

Applications

Hence, an example particle focusing apparatus comprises a substrate, at least one surface acoustic wave (SAW) generator operable to generate a standing surface acoustic wave (SSAW) in the substrate; and a channel configured to receive a fluid sample including particles, the channel having a particle focusing region located on a portion of the substrate in which the SSAW is generated. Methods and apparatus according to embodiments of the present invention may further include particle characterization, for example using radiation directed at a focused particle flow, or focused particles within a static fluid sample.

Particle characterization may include apparatus and methods for particle detection, particle analysis, particle counting, and combinations of such approaches. For example, a radiation source may be used to direct radiation towards focused particles within a fluid medium. The integration of particle focusing with analytical methods and apparatus allows improved methods and apparatus for particle characterization. Particles may be suspended in the fluid medium, which may be a sample flow through the channel.

For example, the integration of microfluidics devices with single microparticle detection techniques allows improved microparticle characterization. Examples of the present invention include apparatus and methods for flow cytometry, and apparatus for counting, analysis, and sorting of microparticles in a sample flow. Microparticles may be defined as particles having a dimension of less than 1 mm, in particular less than 500 microns, and more particularly less than 100 microns. Microparticles may include cells, molecules, biomolecules, and the like.

Example apparatus include miniaturized platforms for flow cytometry and fluorescence activated cell sorting (FACS). In these applications, fluorescently labeled microparticles (e.g., cells) are excited by a laser that is focused on a small volume within a microchannel to allow for accurate detection and sorting. Particle focusing allows substantially all of the particles to be detected or counted. The dimensions of a laser's focal volume are often appreciably smaller than those of a microchannel. Without focusing, many species of interest pass by the focal volume without being exited or detected. Microparticle focusing also facilitates particle sorting by lining up the particles in the microfluidic channel. Other applications include flow cytometry, cell sorting/counting, and tissue engineering.

Microparticle focusing techniques such as those described here can constrain the distribution of the microparticles so that substantially all or most the particles can be registered by the detector. Focusing can be in 2 or 3 dimensions, 3D focusing can be achieved using SSAW alone, or using SSAW in combination with one or more other focusing techniques.

Other particle focusing techniques include hydrodynamic focusing, electro-kinetic focusing, electrophoresis (EP), and dielectrophoresis (DEP) focusing. In hydrodynamic focusing, the microparticle suspension is constrained in the middle of the channel by outer sheath flows of higher flow rates. The introduction of excessive sheath solution, however, dilutes and disperses the sample. Other techniques, such as electrokinetic focusing or DEP focusing, focus the microparticles by creating a force field applied directly to microparticles themselves. These methods do not require an additional sheath solution, but they are only applicable to certain types of microparticles: electro-kinetic focusing is only for charged species, and DEP focusing relies on the polarizability of the particles.

Examples of the present invention include improved flow cytometers and other cell characterization devices, improved molecule detection devices, other analyte characterization devices, analyte sorting devices, genetic analysis devices, and the like. A SAW (SSAW or propagating SAW) can be used for dynamic particle separation and subsequent sorting. A particle may be a molecule (such as a polymer, macromolecule, or biomolecule), biological structure (such as a cell, for example a blood cell), particle (of any type), micelle, droplet of different density from a host fluid, and the like.

A radiation beam, such as a laser, may be directed through the narrowed portions of a focused particle flow. Particles may be characterized using radiation scattering (e.g. light scattering), absorption, fluorescence, luminescence, or other particle-related property which may be monitored.

Particles may be labeled, for example with a fluorescent marker, or otherwise functionalized. For example, biological macromolecules may be fluorescently tagged and detected in the sample flow. After detection, particles may be sorted using one or more of various techniques, e.g. by electrostatic methods.

An apparatus may be a planar microfluidic device. A channel may have a lower wall parallel to and proximate the substrate, opposed side walls, and an upper wall. A channel width and/or height may be in the range 100 nm-1 mm, for example in the range 1 micron-500 microns.

A piezoelectric substrate may comprise lithium niobate, lithium tantalate, lead zirconium titanate, polymer such as polyvinylidene fluoride (PVdF) or other fluoropolymer, quartz, or other material. An IDT can also form part of a sensor system, for example using time gating or monitoring drive signal properties. In some examples, the substrate may provide a wall of the flow channel, or the flow channel may have a wall bonded to the substrate.

Example apparatus may include a radiation source (such as a laser), and a radiation beam may be directed into the channel within or close to a region of hydrodynamic focus. One or more detectors may be configured to receive detected radiation, which may comprise transmitted, scattered and/or fluorescent radiation. An electronic circuit, such as a computer, may be used to analyze detector signals, so as to determine properties of the particles. For example, cell dimensions and other properties may be determined, and particles may be imaged, reacted, or otherwise processed.

Examples of the present invention include high-throughput cell cytometers, single-molecule fluorescent spectrometers, genetic analyzers, fluorescence-activated cell sorters, and other applications. In some examples, particles having detected properties may be counted, extracted, sorted, or otherwise processed. In some examples, a plurality of radiation sources, such as lasers, and associated detectors may be used.

In some examples, a sample flow is not required and particle focusing can occur in a static host fluid medium. A SSAW can induce particle focusing in any suitable sample region. There may be one or more regions of particle focus.

Examples of the present invention include using a SSAW to modify the spatial distribution of particles within a fluid, for example concentrating the spatial distribution within a focus region within a microchannel fluid flow. The focus region has an enhanced particle concentration relative to the remainder of the fluid, in some examples enhanced by at least one order of magnitude, and in some examples at least two orders of magnitude. Prior to focusing, the particle suspension may be generally uniform within a fluid medium.

Examples of the present invention include novel methods and apparatus to implement particle focusing (e.g. focusing of microparticles and/or nanoparticles using SSAWs. An example apparatus comprises a single-layer planar microfluidic device, which may be fabricated via a standard soft-lithography technique. Examples of the present invention allow significant simplification of device fabrication, much lower power consumption, and reduction of cost.

Comparison with Bulk Acoustic Waves (BAW)

Acoustic waves generate pressure gradients in liquid that can be used to manipulate suspended particles or liquid medium. Acoustic-based methods are useful for on-chip microparticle focusing, since they do not need a sheath solution and can be used to focus virtually any microparticles. A microparticle may be a particle having a cross-sectional dimension, such as a diameter, less than 1 mm, for example in the range 0.1 microns-500 microns, more particularly 0.5 micron-100 microns. The term microparticle, as used herein, may include nanoparticles.

Acoustophoresis allows the separation of microparticles of different sizes and densities in microfluidic channels using standing bulk acoustic waves (BAW). However, the formation of a standing BAW in single-transducer resonating systems requires that the channel material possess excellent acoustic reflection properties. Soft polymer materials such as polydimethylsiloxane (PDMS) that are commonly used in microfluidic applications have poor reflection properties. Therefore, the requirement of high acoustic reflection makes it challenging to implement these single-transducer BAW-based techniques with fast prototyping methods, such as soft lithography, that are widely used in microfluidics.

A dual-transducer non-resonating BAW-based system may be compatible with soft lithography techniques. However, SSAW based approaches may be used in relatively simple designs.

SAW Transducers

Examples of the present invention include a standing surface acoustic wave generator operable to generate a standing surface acoustic wave (SSAW) within a region of the substrate. An example SSAW generator is a pair of SAW generators, spaced apart on the substrate with the SSAW region formed between them. The channel can be configured so that the fluid sample (within the particle focusing region) is over the SSAW region of the substrate.

An example SAW generator is an IDT, which may be formed as electrodes on the substrate. For example, metal films may be deposited or otherwise formed as interdigitated electrodes on a piezoelectric substrate.

An IDT may be formed using patterned electrodes on a piezoelectric substrate. The same substrate may be used for the IDT and for supporting the channel, for example the substrate providing the base of the channel. In some examples, IDTs using a piezoelectric substrate may be mounted on a second substrate used for the channel base.

A SAW (e.g. a SSAW) can be induced in a substrate by any appropriate transducer, for example a transducer supported by the substrate or formed using the substrate material. In some examples, one or more bulk acoustic waves can be used to induce formation of a SAW. In some examples, a SAW generator formed using a piezoelectric substrate may be used to generate a SAW in another substrate, a part of which is proximate a fluid channel. In other examples, a transducer in mechanical connection with a channel wall is used to generate a SAW (e.g. a SSAW) in the channel wall.

Substrates

The substrate may comprise a piezoelectric material, and may comprise, for example, a niobate (such as an alkali metal niobate, e.g. lithium niobate, sodium niobate, sodium potassium niobate, barium sodium niobate, and the like), a titanate (such as barium titanate, lead zirconate titanate, and the like), a tantalate (such as an alkali metal tantalate such as lithium tantalate), quartz, ferrite, vinylidene polymer such as polyvinylidene fluoride (PVDF) and derivatives thereof, other ferroelectric material, or any other piezoelectric material. The substrate for may comprise one or more piezoelectric materials.

Channels

Channels may be microchannels, for example having at least one cross-sectional dimension less than 1 millimeter, such as less than 500 microns, and more particularly less than 100 microns. For example, the height (normal to the substrate) and/or width of a generally rectangular channel, or other dimensional parameter such as diameter, may be in the range 1 micron-1 millimeter, and more particularly in the range 10 microns-100 microns. The cross-section may be generally rectangular, though other cross-sectional geometries are possible. The channel dimensions are not limited to these dimensions, but may be limited by the extent of the SSAW propagation area on a substrate.

Channels may be formed using a molded or otherwise formed in a polymer or other material. For example, a trench or other structure may be formed in a polymer (or other material), and then placed against the substrate to form a channel. The polymer may be a siloxane polymer such as a polydimethylsiloxane (PDMS). However, other polymers may be used to fabricate the formed element through which the channel passes, such as other silicone polymers, or other polymers having desired mechanical, chemical, and/or physical properties. For example, a polymer may be selected so as to be effectively transparent to radiation used to analyze, count, or otherwise characterize the particles in the channel. The channel may be formed in a soft polymer, i.e. a polymer in which features can be formed by soft lithography.

In some examples, the polymer formed element may be disposable, for example for a flow cytometer or other bioparticle characterization apparatus. The channel may be enclosed by the formed element, and acoustic waves coupled to the fluid sample within the channel by the material of the formed element.

A channel may be formed by placing a polymer element including a trench against the substrate. In this case, the side walls and top of the channel are provided by the polymer, and the channel base is the substrate. The side walls may be quite thick over some of the channel length. However, an opening or cut-away portion of the polymer may narrow the side walls within the SSAW propagation area. Channels can be formed by other methods if desired.

Example apparatus and methods of focusing particles within a fluid sample include introducing the fluid sample to a channel proximate a substrate, and generating a surface acoustic wave (SAW) on the substrate. A SAW is an acoustic wave propagating along a substrate surface, and interaction of two or more SAWs may be used to generate a SSAW within a region of the substrate surface. Part of the SSAW region of the substrate surface may be in mechanical communication with the fluid sample, for example in contact with the fluid sample within the channel. A surface supporting a SAW may provide a bounding surface of the channel.

The polymer or other material used to form the channel may be partially removed around the SSAW region, for example using cut-outs to leave narrowed channel boundary walls, so as to reduce attenuation the SSAW generation. Windows may be provided to the channel for radiation incidence and collection, for example for particle characterization. The term "acoustic", in connection with SAW or SSAW, imposes no frequency limits.

An apparatus may further include electronic circuitry for driving the transducers, receiving and analyzing sensor signals. A particle characterization device may include a radiation source, sensor, and an analysis electronic circuit for characterizing the particles. Particles may be sorted using various mechanisms, for example by inducing an electrostatic charge in a detected particle as the particle leaves the channel.

Patents, patent applications, or publications mentioned in this specification are incorporated herein by reference to the same extent as if each individual document was specifically and individually indicated to be incorporated by reference. In particular, the entire contents of Provisional Application Ser. No. 61/200,958, filed Dec. 5, 2008, are incorporated herein by reference.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

Having described our invention, we claim:

1. An apparatus for particle focusing of particles within a fluid sample, the apparatus comprising:
   a substrate, having a substrate surface;
   a surface acoustic wave generator, operable to generate a surface acoustic wave (SAW) within a SAW region of the substrate surface; and
   a channel, configured to receive the fluid sample,
   the channel having a particle focusing portion proximate the SAW region of the substrate,
   the particle focusing portion providing focused particles within the fluid sample when the SAW is generated.

2. The apparatus of claim 1, the surface acoustic wave generator comprising an interdigitated transducer including interdigitated electrodes supported by the substrate,
   the substrate being a piezoelectric substrate.

3. The apparatus of claim 1, the apparatus comprising a pair of spaced apart surface acoustic wave generators operable to generate a standing surface acoustic wave (SSAW) within a SSAW region of the substrate surface,
   the SSAW region being located between the pair of surface acoustic wave generators,
   the particle focusing portion being proximate the SSAW region of the substrate.

4. The apparatus of claim 1, the apparatus being a microfluidic device,
   the channel being a microchannel having at least one cross-sectional dimension less than 1 mm,
   the particles being microparticles having a cross-sectional dimension less than 100 microns.

5. The apparatus of claim 1, further including a particle characterization device, operable to characterize focused particles.

6. The apparatus of claim 5, wherein the apparatus is a cytometer, fluorescence particle detector, particle sorter, fluorescent spectrometer, or genetic analyzer.

7. An apparatus for particle focusing of particles within a fluid sample, the apparatus comprising:
   a substrate;
   a first surface acoustic wave generator;
   a second surface acoustic wave generator,
   the first and second surface acoustic wave generators being configured to generate a standing surface acoustic wave (SSAW) within a SSAW region of the substrate; and
   a channel, configured to receive a fluid sample including particles, the channel having a particle focusing portion proximate the SSAW region of the substrate,
   the apparatus being operable to provide focused particles within the fluid sample when the fluid sample is introduced into the channel and the SSAW is generated.

8. The apparatus of claim 7, the substrate being a piezoelectric substrate,
   the first and second surface acoustic wave generators each comprising electrodes supported by the substrate.

9. The apparatus of claim 7, the substrate forming a wall of the channel.

10. The apparatus of claim 7, the apparatus being a microfluidic device,
    the channel being a microchannel,
    the microchannel having at least one cross-sectional dimension less than 1 mm.

11. The apparatus of claim 10, the channel being a flow channel configured to receive a sample fluid flow,
    the particle focusing portion of the flow channel being operable to induce a focused particle stream within the sample fluid flow.

12. The apparatus of claim 7, further including a particle characterization device for characterizing the focused particles.

13. The apparatus of claim 12, the particle characterization device including:
    a radiation source, operable to provide an radiation beam incident on the focused particles within the microchannel; and
    a radiation detector, operable to receive radiation from the focused particles.

14. The apparatus of claim 13, the radiation detector operable to receive fluorescence from the focused particles,
    the apparatus being a fluorescence particle detector or fluorescence spectrometer.

15. The apparatus of claim 12, the apparatus being a flow cytometer, particle detector, particle sorter, particle counter, or particle analyzer.

16. The apparatus of claim 7, wherein the particles are microparticles having a diameter of less than 500 microns.

17. The apparatus of claim 16, wherein the microparticles are biomolecules or cells.

18. A method of focusing particles within a fluid sample including the particles, the method comprising:
    locating the fluid sample proximate a substrate; and
    generating a standing surface acoustic wave (SSAW) within the substrate,
    the SSAW inducing pressure forces within the fluid so as to focus the particles within the fluid sample.

19. The method of claim 18, the fluid sample being a sample flow directed along a flow channel,
    the flow channel being supported by the substrate,
    the flow channel being a microchannel within a microfluidic device,
    the method being a method of particle characterization.

20. The method of claim 18, the method being method of three-dimensional particle focusing,
   the particles being focused in a first plane parallel to the substrate, and further being focused in a second plane normal to the substrate.

* * * * *

UNITED STATES PATENT AND TRADEMARK OFFICE
CERTIFICATE OF CORRECTION

PATENT NO.       : 8,573,060 B2
APPLICATION NO.  : 12/631059
DATED            : November 5, 2013
INVENTOR(S)      : Tony Jun Huang et al.

Page 1 of 1

It is certified that error appears in the above-identified patent and that said Letters Patent is hereby corrected as shown below:

In the Claims

Column 16, line 39: After "provide" replace "an" with --a--.

Signed and Sealed this
Thirtieth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,573,060 B2
APPLICATION NO.   : 12/631059
DATED             : November 5, 2013
INVENTOR(S)       : Tony Jun Huang et al.

Page 1 of 1

It is certified that error appears in the above-identified patent and that said Letters Patent is hereby corrected as shown below:

Title page item (75): Replace "Jingie Shi" with --Jinjie Shi--

Signed and Sealed this
Seventeenth Day of November, 2015

Michelle K. Lee
*Director of the United States Patent and Trademark Office*